United States Patent [19]

Hadley et al.

[11] Patent Number: 4,560,757

[45] Date of Patent: Dec. 24, 1985

[54] 9-AZABICYCLO(3.3.1) NONANE INTERMEDIATES FOR COMPOUNDS USEFUL IN THE TREATMENT OF CNS DISORDERS

[75] Inventors: Michael S. Hadley, Sawbridgeworth; Francis E. Blaney, London, both of England

[73] Assignee: Beecham Group p.l.c., England

[21] Appl. No.: 530,513

[22] Filed: Sep. 9, 1983

Related U.S. Application Data

[62] Division of Ser. No. 432,028, Sep. 30, 1982, Pat. No. 4,472,413.

[30] Foreign Application Priority Data

| Oct. 1, 1981 | [GB] | United Kingdom | 8129717 |
| Nov. 28, 1981 | [GB] | United Kingdom | 8135970 |
| Jun. 19, 1982 | [GB] | United Kingdom | 8217835 |
| Jul. 7, 1982 | [GB] | United Kingdom | 8219721 |

[51] Int. Cl.[4] .......................................... C07D 457/14
[52] U.S. Cl. ................................. 546/112; 546/183
[58] Field of Search ................................. 546/112, 183

[56] References Cited

U.S. PATENT DOCUMENTS 4,273,778 6/1981 Hadley et al. .................... 546/112

OTHER PUBLICATIONS

Schulz et al.; Arzneim–Forsch, vol. 26(5a) (1976), pp. 960–974.

Primary Examiner—Henry R. Jiles
Assistant Examiner—Bernard I. Dentz
Attorney, Agent, or Firm—Jacobs & Jacobs

[57] ABSTRACT

Compounds of formula (I):

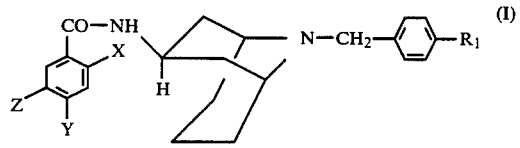

wherein X is methoxy or ethoxy, Y is amino or $C_{1-6}$ alkanoylamino, Z is hydrogen, chloro or bromo and $R_1$ is methyl, chloro or fluoro, have anti-psychotic activity, and are useful in the treatment of CNS disorders. Intermediates for the above compounds are also disclosed.

1 Claim, No Drawings

9-AZABICYCLO(3.3.1) NONANE INTERMEDIATES FOR COMPOUNDS USEFUL IN THE TREATMENT OF CNS DISORDERS

CROSS-REFERENCE

This is a division of Ser. No. 432,028 filed Sept. 30, 1982 now U.S. Pat. No. 4,472,413.

This invention relates to novel benzamides, to pharmaceutical compositions containing them, to processes and intermediates for their preparation, and to their use in the treatment of psychosis.

South African Pat. No. 80/0160 discloses inter alia compounds of formula (A), and their pharmaceutically acceptable salts:

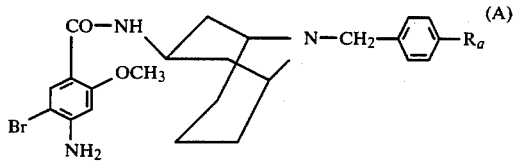

wherein $R_a$ is a lower alkyl, trifluoromethyl or cyano group or an atom of chlorine, bromine of fluorine. Such compounds are described as having neuroleptic properties.

European Patent Publication No. 13138 and U.S. Pat. No. 4,273,778 disclose benzamides of formula (B), and their pharmaceutically acceptable salts, N-oxides and hydrates thereof:

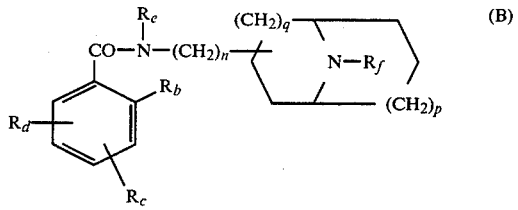

wherein:

$R_b$ is a $C_{1-6}$ alkoxy group;

$R_c$ and $R_d$ are the same or different and are hydrogen, halogen, $CF_3$, $C_{2-7}$ acylamino, or amino, aminocarbonyl or aminosulphone optionally substituted by one or two $C_{1-6}$ alkyl groups, $C_{1-6}$ alkylsulphone or nitro;

$R_e$ is hydrogen or $C_{1-6}$ alkyl;

$R_f$ is $C_{1-7}$ alkyl or a group $-(CH_2)_sR_g$ where s is 0 to 2 and $R_g$ is a $C_{3-8}$ cycloalkyl group, or a group $-(CH_2)_tR_h$ where t is 1 or 2 and $R_h$ is $C_{2-5}$ alkenyl or a phenyl group optionally substituted by one or two substituents selected from $C_{1-6}$ alkyl, $C_{1-4}$ alkoxy, trifluoromethyl and halogen; and n, p and q are independently 0 to 2.

The benzamides of formula (B) are described as dopamine antagonists and are useful in the treatment of emesis. They are also described, depending on their balance between peripheral and central action on the nervous system, as being useful in the treatment of disorders relating to impaired gastro-intestinal motility, such as retarded gastric emptying, dyspepsia, flatulence, oesphagal reflux and peptic ulcer, and/or in the treatment of disorders of the central nervous system, such as psychosis.

A number of novel benzamides have now been discovered which fall within the scope of the aforementioned European patent publication and U.S. patent and which have a norgranatyl side chain containing a p-methyl, p-chloro or p-fluorobenzyl substituent on the bridgehead nitrogen atom. Such benzamides have particularly advantageous anti-psychotic activity. They also have a low level of side effects, such as extrapyramidal effects, and a prolonged duration of action. They are therefore useful in the treatment of psychosis.

Accordingly, the present invention provides a compound of formula (I), or a pharmaceutically acceptable salt or solvate thereof:

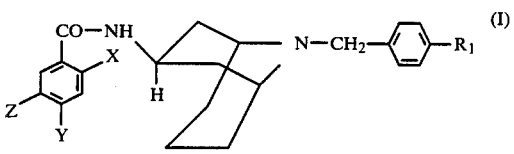

wherein X is methoxy or ethoxy, Y is amino or $C_{1-6}$ alkanoylamino, Z is hydrogen, chloro or bromo and $R_1$ is methyl, chloro or fluoro.

Preferably, X is methoxy.

When Y is $C_{1-6}$ alkanoylamino, it is preferably acetylamino. However, Y is preferably amino.

Preferably, Z is bromo or, in particular, chloro.

Included within formula (I) are the compounds; 4-amino-5-chloro-2-methoxy-N-(3'β-[9'-(4-methylbenzyl)-9'-azabicyclo-[3.3.1]-nonyl])benzamide; 4-amino-5-chloro-2-methoxy-N-(3'β-[9'-(4-chlorobenzyl)-9'-azabicyclo-[3.3.1]-nonyl])benzamide; 4-amino-5-chloro-2-methoxy-N-(3'β-[9'-(4-fluorobenzyl)-9'-azabicyclo-[3.3.1]-nonyl])benzamide; 4-amino-5-bromo-2-methoxy-N-(3'β-[9'-(4-fluorobenzyl)-9'-azabicyclo-[3.3.1]-nonyl])benzamide; 4-acetylamino-5-chloro-2-methoxy-N-(3'β-[9'-(4-fluorobenzyl)-9'-azabicyclo[3.3.1]nonyl])benzamide; 4-acetylamino-5-chloro-2-methoxy-N-(3'β-[9'-(4-chlorobenzyl)-9'-azabicyclo[3.3.1]nonyl])benzamide; 4-acetylamino-5-chloro-2-methoxy-N-(3'β-[9'-(4-methylbenzyl)-9'-azabicyclo[3.3.1]nonyl])benzamide; 4-acetylamino-2-methoxy-N-(3'β-[9'-(4-fluorobenzyl)-9'-azabicyclo[3.3.1]nonyl])benzamide; 4-amino-2-methoxy-N-(3'β-[9'-(4-fluorobenzyl)-9'-azabicyclo[3.3.1]nonyl])-benzamide; and their pharmaceutically acceptable salts and solvates thereof.

The most preferred compounds of formula (I) are the compounds, wherein $R_1$ is fluoro and their pharmaceutically acceptable salts and solvates.

The pharmaceutically acceptable salts of the compound of formula (I) include acid addition salts with conventional pharmaceutically acceptable acids, such as hydrochloric, hydrobromic, phosphoric, sulphuric, citric, tartaric, lactic and acetic acid.

The solvates of the compounds of formula (I) include hydrates.

The invention also provides a process of preparing a compound of formula (I), or a pharmaceutically acceptable salt or solvate thereof, which comprises reacting a compound of formula (II):

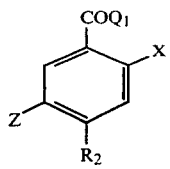

(II)

wherein X and Z are as defined hereinbefore, $R_2$ is Y or a protected amino group, and $Q_1$ is a leaving group, with a compound of formula (III):

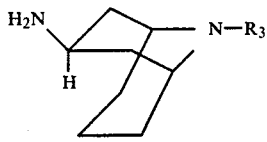

(III)

wherein $R_3$ is a protecting group or p-methylbenzyl, p-chlorobenzyl or p-fluorobenzyl; in the case where $R_2$ is a protected amino group, removing the protecting group; in the case where $R_3$ is a protecting group, removing the protecting group and reacting the secondary amine with a compound of formula (IV):

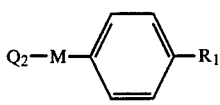

(IV)

wherein $Q_2$ is a leaving group, M is CO or $CH_2$ and $R_1$ is as hereinbefore defined, and when M is CO, reducing the resulting N-benzoyl compound to give the corresponding N-benzyl compound; in the case where $R_2$ is Y, optionally converting the amino group or the $C_{1-6}$ alkanoylamino group into the other; and optionally forming a pharmaceutically acceptable salt or solvate thereof.

The leaving group $Q_1$ is a group that is readily displaceable by a nucleophilic primary amine such that an amido linkage can be formed between the compounds of formula (II) and (III). It may be displaced in the form of an anion or in the form of a condensation by-product.

Examples of the leaving group $Q_1$ include hydroxy, halogen, acyloxy and activated hydrocarbyloxy.

When the leaving group is hydroxy, then the reation is preferably carried out in an inert non-hydroxylic solvent, such as benzene, toluene, dichloromethane, dimethylformamide or diethyl ether in the presence of a dehydrating catalyst, such as a carbodiimide, for example dicyclohexylcarbodiimide. The reaction may be carried out at any non-extreme temperature, such as $-10°$ to $100°$ C., for example, $0°$ to $80°$ C.

When the leaving group is halogen, such as chloro or bromo, then the reaction is preferably carried out at non-extreme temperatures in an inert non-hydroxylic solvent, such as benzene, toluene, dichloromethane or diethyl ether. It is also preferably carried out in the presence of an acid acceptor, such as an organic base, in particular a tertiary amine, such as triethylamine, trimethylamine, pyridine or picoline, a number of which can also function as the solvent. Alternatively, the acid acceptor can be inorganic, such as calcium carbonate, sodium carbonate or potassium carbonate.

When the leaving group is acyloxy, such as $C_{1-4}$ alkanoyloxy, then the reaction is preferably carried in substantially the same manner as if the leaving group were hydroxy.

When the leaving group is acyloxy, such as $C_{1-4}$ alkoxycarbonyloxy, then the reaction is preferably carried out in an inert solvent, such as methylene chloride, at a non-extreme temperature in the presence of an acid acceptor, such as triethylamine.

When the leaving group is activated hydrocarbyloxy then the reaction is preferably carried out in an inert polar solvent, such as dimethylformamide. It is also preferred that the activated hydrocarbyloxy group is a pentachlorophenyl ester and that the reaction is carried at ambient temperature.

Preferably $Q_1$ is hydroxy, chloro or, in particular, $C_{1-4}$ alkoxycarbonyloxy, such as ethoxycarbonyloxy.

A protected amino group for $R_2$ is an amino group substituted by a protecting group. Examples of such protecting groups include $C_{1-6}$ alkanoyl groups, for example acetyl, propionyl, n- and iso-butyryl and 2,2-dimethylpropanoyl, or benzoyl optionally substituted in the phenyl ring by one or two substituents selected from $C_{1-4}$ alkyl, $C_{1-4}$ alkoxy, trifluoromethyl and nitro, or $C_{1-4}$ alkoxycarbonyl, for example tert-butoxycarbonyl.

Examples of protecting groups for $R_3$, when so defined, include those for $R_2$, when a protected amino group. Additionally, $R_3$ may also be a benzyl group optionally substituted as defined above for a benzoyl protecting group.

The removal of the protecting group $R_3$ and/or the removal of the protecting group from the protected amino group $R_2$ are/is achieved in accordance with known procedures. For example, the removal of a $C_{1-6}$ alkanoyl or an optionally substituted benzoyl protecting group may be achieved by acid or base hydrolysis, preferably at an elevated temperature. Additionally, the removal of a $C_{1-4}$ alkoxycarbonyl protecting group may be achieved with trifluoroacetic acid. And the removal of an optionally substituted benzyl protecting group may be achieved by hydrogenolysis, for example using a transition metal catalyst, such as platinum or palladium on charcoal, at or above atmospheric pressure in a solvent, such as ethanol, at ambient temperature.

Whenever $R_2$ is a protected amino group and $R_3$ is a protecting group, it is preferred that the protecting groups are independently removable. For example, one of the protecting groups may be a $C_{1-4}$ alkanoyl group, such as an acetyl group, removable by acid or base hydrolysis and the other may be a benzyl group removable by catalytic hydrogenolysis. Conveniently $R_3$ is benzyl and $R_2$ is $C_{1-4}$ alkanoylamino, such as acetylamino.

It is also preferred, whenever $R_2$ is a protected amino group and $R_3$ is a protecting group, that the protecting group $R_3$ is removed and the resulting secondary amine reacted with a compound of formula (IV) prior to removal of the protecting group of the protected amino group $R_2$.

The leaving group $Q_2$ of formula (IV) is a group that is readily displaceable by a nucleophilic secondary amine such that a tertiary amine or amide can be formed. Examples of such leaving groups, when M is $CH_2$, include chloro, bromo, iodo, mesyloxy and tosyloxy, and, when M is CO, include the groups listed hereinbefore in regard to the leaving group $Q_1$. Particularly preferred examples of $Q_2$ include chloro, bromo and iodo.

The reaction of the secondary amine with a compound of formula (IV), wherein M is $CH_2$, may be carried out under conventional aralkylation conditions, for example, in an inert solvent, such as dimethyl formamide in the presence of an acid acceptor, such as potassium carbonate. Generally, the reaction is carried out at a non-extreme temperature, such as at ambient temperature or at a slightly elevated temperature.

The reaction of the secondary amine with a compound of formula (IV), wherein M is CO, may be carried out under conventional aroylation conditions, for example, the conditions described hereinbefore for the reaction between compounds of formula (II) and (III). The resulting N-benzoyl compound may be reduced to give the corresponding N-benzyl compound in accordance with known reducing procedures, for example by reduction with lithium aluminium hydride or diborane. In this regard, the reaction with the benzoyl derivative of formula (IV) and the subsequent reduction can conveniently be carried out in a single operation using sodium cyanoborohydride under weakly acidic conditions.

It is however more preferred that $R_2$ is an amino group or a protected amino group and $R_3$ is p-methylbenzyl, p-chlorobenzyl or in particular p-fluorobenzyl. In this way, the additional steps of removing the protecting group $R_3$ and reacting the resulting secondary amine with a compound of formula (IV) are avoided.

Conversion of a compound of formula (I), wherein $R_2$ is amino, into a corresponding compound of formula (I), wherein $R_2$ is $C_{1-6}$ alkanoylamino, may be carried out in accordance with known procedures, for example by reaction with an acylating derivative, such as the anhydride or acid halide, of the appropriate $C_{1-6}$ alkanoic acid.

It will be appreciated from the foregoing that the compounds of formula (I), wherein $R_2$ is amino or $C_{1-6}$ alkanoylamino, can function as useful intermediates as well as anti-psychotic agents.

The compounds of formula (II) and (IV) are known or can be made analogously to the preparation of known compounds.

The compounds of formula (III) can be prepared by reduction of a compound of formula (V):

(V)

wherein $R_3$ is hereinbefore defined.

In order preferentially to obtain the β-isomer of formula (III), it is preferred that the reduction is carried out with an alkali metal, such as sodium, and a $C_{1-6}$ alkanol, such as amyl alcohol. Reducing agents which give mixtures of α- and β-isomers may also be used as the desired β-isomer can be separated from the mixture by conventional techniques. However, any such separation is preferably carried out later in the synthesis when the isomers are easier to handle. It is particularly preferred that the separation is carried out on the product of the reaction between a compound of formula (II), wherein $R_2$ is a protected amino group, such as $C_{1-6}$ alkanoylamino, e.g. acetylamino, and a compound of formula (III).

The compounds of formula (V) can be prepared by reaction of a compound of formula (VI):

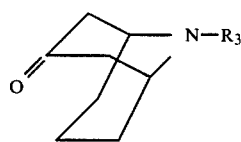
(VI)

wherein $R_3$ is as hereinbefore defined, with hydroxylamine.

The compounds of formula (VI), wherein $R_3$ is p-methylbenzyl, p-chlorobenzyl or p-fluorobenzyl, or is a benzyl protecting group optionally substituted as hereinbefore defined, can be prepared by reaction of a compound of formula (VII):

$H_2N-R_3$ (VII)

wherein $R_3$ is as defined, with glutaric dialdehyde and 1,3-acetone dicarboxylic acid. On the other hand, compounds of formula (VI), wherein $R_3$ is a protecting group that gives rise to a carbonyl function adjacent to the nitrogen atom, such as $C_{1-6}$ alkanoyl, benzoyl optionally substituted as hereinbefore defined, or $C_{1-4}$ alkoxycarbonyl, are prepared by removal of the benzyl protecting group optionally substituted as hereinbefore defined from a compound of formula (VI), wherein $R_3$ is so defined, and then converting the secondary amine to a compound of formula (VI), wherein $R_3$ is a carbonyl-containing protecting group as defined.

The compounds of formula (VII) are known or can be prepared analogously to the preparation of known compounds.

During the reduction of compounds of formula (V), when $R_3$ is p-chlorobenzyl or p-fluorobenzyl, some undesired hydrogenolysis of the carbon-chloro or carbon-fluoro bond appears to occur. When $R_3$ is p-chlorobenzyl it appears to occur to a greater extent than when $R_3$ is p-fluorobenzyl although the desired products can still be obtained, albeit in low yields using conditions that are favourable to the reduction of the oximo double bond and less favourable to hydrogenolysis of the carbon-chloro or carbon-fluoro bond, such as a shorter reaction time and lower temperature.

Because of the occurrence of the above mentioned side-reaction, the present invention provides an alternative process for the preparation of a compound of formula (III), which comprises the removal of the protecting group from a compound of formula (VIII):

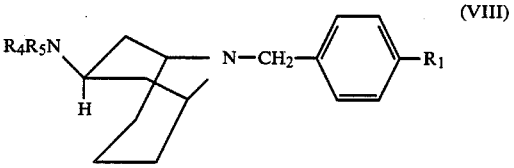
(VIII)

wherein $R_1$ is as hereinbefore defined and one of $R_4$ and $R_5$ is a monovalent protecting group and the other is hydrogen or $R_4$ and $R_5$ together are a divalent protecting group.

The protecting group is such that its removal can be carried out under conditions that will not significantly affect any other part of the compound. In particular, there should be no significant removal of the p-substituted benzyl moiety. A particularly preferred example of a monovalent protecting group is $C_{1-6}$ alkanoyl, such as acetyl, which can be removed in the desired manner by acid or base hydrolysis. An example of a divalent protecting group is phthaloyl which can be removed in the desired manner by base hydrolysis.

This alternative process is favoured for the preparation of those compounds of formula (III), wherein $R_1$ is chloro or fluoro. The other process is favoured for the preparation of those compounds of formula (III), wherein $R_3$ is other than p-chlorobenzyl or p-fluorobenzyl, in particular wherein $R_3$ is p-methylbenzyl.

The compounds of formula (VIII) can be prepared by reaction of a compound of formula (IX):

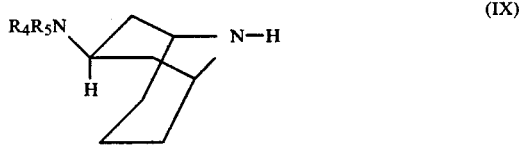

wherein $R_4$ and $R_5$ are as hereinbefore defined, with a compound of formula (IV), as hereinbefore defined.

The reaction may be carried out under conventional aralkylation conditions, for example, in an inert solvent, such as dimethylformamide, in the presence of an acid acceptor, such as potassium carbonate.

The compounds of formula (IX) can be prepared by hydrogenolysis of a compound of formula (X):

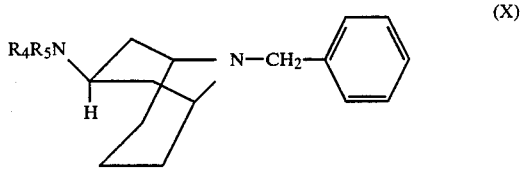

wherein $R_4$ and $R_5$ are as hereinbefore defined.

The hydrogenolysis is conveniently carried out at room temperature and atmospheric pressure using 10% palladium on charcoal.

The compounds of formula (X) can be prepared by reacting the compound of formula (XI):

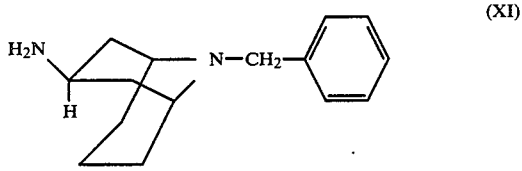

with a reagent that will monovalently or divalently protect the primary amine.

The compound of formula (XI) is known.

The present invention provides another process of preparing a compound of formula (I), wherein Z is chloro or bromo, or a pharmaceutically acceptable salt or solvate thereof, which comprises chlorinating or brominating a compound of formula (XII):

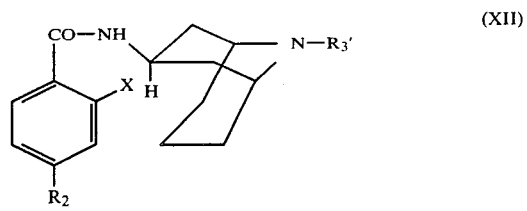

wherein X and $R_2$ are as defined hereinbefore and $R_3'$ is hydrogen or $R_3$ as defined hereinbefore; in the case where $R_2$ is a protected amino group, removing the protecting group; in the case where $R_3'$ is $R_3$ and is a protecting group, removing the protecting group to give a compound of formula (XII), wherein $R_3'$ is hydrogen; in the case where $R_3'$ is hydrogen, reacting the secondary amine with a compound of formula (IV), as hereinbefore defined, and when M is CO, reducing the resulting N-benzoyl compound to give the corresponding N-benzyl compound; in the case where $R_2$ is Y, optionally converting the amino group or the $C_{1-6}$ alkanoylamino group into the other; and optionally forming a pharmaceutically acceptable salt or solvate thereof.

The chlorination or bromination is preferably carried out under acidic conditions using, for example, acetic acid.

It is greatly preferred that $R_2$ in formula (XII) is a protected amino group, such as $C_{1-6}$ alkanoylamino, since otherwise dichlorination or dibromination could occur.

The present invention additionally provides a process of preparing a compound of formula (I), or a pharmaceutically acceptable salt of solvate thereof, which comprises reducing a compound of formula (XIII):

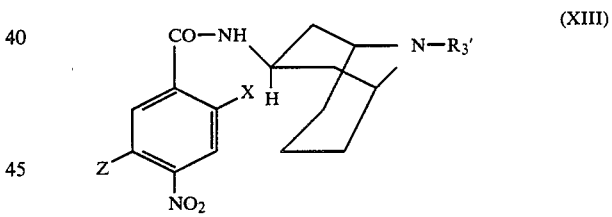

wherein X and Z and $R_3'$ are as defined hereinbefore; in the case where $R_3'$ is $R_3$ and is a protecting group, removing the protecting group to give a compound of formula (XIII), wherein $R_3'$ is hydrogen; in the case where $R_3'$ is hydrogen, reacting the secondary amine with a compound of formula (IV), as hereinbefore defined, and when M is CO, reducing the resulting N-benzoyl compound to give the corresponding N-benzyl compound; optionally converting the primary amino group to a $C_{1-6}$ alkanoylamino group; and optionally forming a pharmaceutically acceptable salt or solvate thereof.

The reduction may be carried out with stannous chloride and concentrated hydrochloric acid or with hydrogen and Raney nickel.

The present invention further provides a process of preparing a compound of formula (I), or a pharmaceutically acceptable salt or solvate thereof, which comprises carrying out a Hoffman degradation on a compound of formula (XIV):

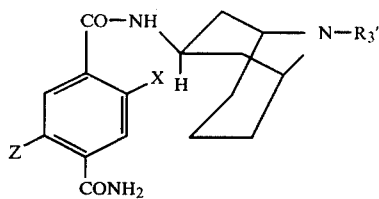

(XIV)

wherein X and Z and $R_3'$ are as hereinbefore defined; in the case where $R_3'$ is $R_3$ and is a protecting group, removing the protecting group to give a compound of formula (XIV), wherein $R_3'$ is hydrogen; in the case where $R_3'$ is hydrogen, reacting the secondary amine with a compound of formula (IV), as hereinbefore defined, and when M is CO, reducing the resulting N-benzoyl compound to give the corresponding N-benzyl compound; optionally converting the primary amino group to a $C_{1-6}$ alkanoylamino group; and optionally forming a pharmaceutically acceptable salt or solvate thereof.

The Hoffman degradation is preferably carried out with a metal hypohalite, such as sodium hypochlorite.

The present invention provides yet a further process of preparing a compound of formula (I), or a pharmaceutically acceptable salt or solvate thereof, which comprises methylating or ethylating a compound of formula (XV):

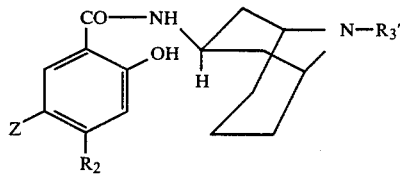

(XV)

wherein Z and $R_2$ and $R_3'$ are as hereinbefore defined; in the case where $R_2$ is a protected amino group, removing the protecting group; in the case where $R_3'$ is $R_3$ and is a protecting group, removing the protecting group to give a compound of formula (XV), wherein $R_3'$ is hydrogen; in the case where $R_3'$ is hydrogen, reacting the secondary amine with a compound of formula (IV), as hereinbefore defined, and when M is CO, reducing the resulting N-benzoyl compound to give the corresponding N-benzyl compound; in the case where $R_2$ is Y, optionally converting the amino group or the $C_{1-6}$ alkanoylamino group into the other; and optionally forming a pharmaceutically acceptable salt or solvate thereof.

The alkylating reaction may be carried out with methyl or ethyl iodide in acetone in the presence of potassium carbonate or with dimethylsulphate in the presence of sodium hydroxide. It is preferred that $R_2$ in formula (XV) is a protected amino group. It is also greatly preferred that $R_3'$ is $R_3$ and is a $C_{1-6}$ alkanoyl or benzoyl protecting group.

Compounds of formulae (XII), (XIII), (XIV) and (XV) can be prepared in an analogous manner to the preparation of compounds of formula (I). However, in the preparation of precursors of the compounds of formula (XV), it may be advisable to protect the hydroxy function during the coupling reaction between compounds analogous to those of formulae (II) and (III) and to protect it if the compounds analogous to those of formula (II), wherein $Q_1$ is other than hydroxy, are prepared from those analogues, wherein $Q_1$ is hydroxy.

Examples of O-protecting groups include those mentioned hereinbefore as protecting groups for $R_2$, when a protected amino group.

There are a number of intermediates of use in the processes as described hereinbefore which are novel and constitute part of the present invention. One class of intermediate is of formula (XVI):

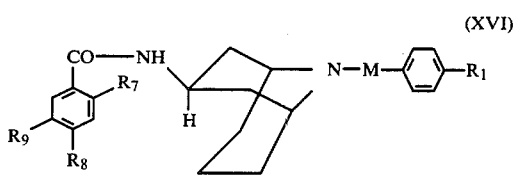

(XVI)

wherein:

$R_7$ is methoxy or ethoxy, $R_8$ is nitro or aminocarbonyl and $R_9$ is hydrogen, chloro or bromo; or $R_7$ is hydroxy, $R_8$ is amino or $C_{1-6}$ alkanoylamino, and $R_9$ is hydrogen, chloro or bromo; and M is $CH_2$ or CO; and $R_1$ is methyl, chloro or fluoro.

Another class is of formula (XVII):

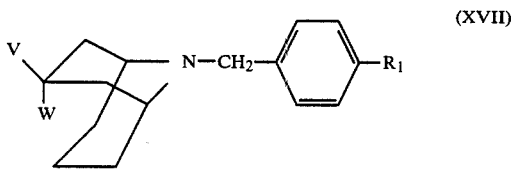

(XVII)

wherein: V is amino or $C_{1-6}$ alkanoylamino and W is hydrogen or V and W together with the carbon atom to which they are attached are an oximino group, and $R_1$ is as hereinbefore defined.

Another useful intermediate is the compound of formula (VI), wherein $R_3$ is p-fluorobenzyl.

The compounds of the present invention are β-isomers, i.e. where the amide linkage joins the bicyclic system, the configuration is of formula (XVIII):

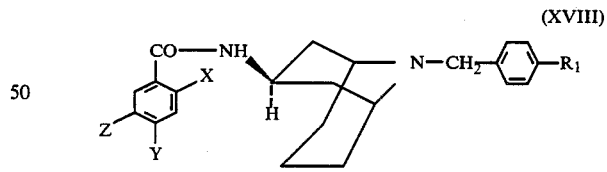

(XVIII)

wherein: X, Y, Z and $R_1$ are as hereinbefore defined.

It is preferred therefore that the intermediate compounds that can also exist in two isomeric forms are used in the β-form as well. However, the intermediate compounds can also be used in mixtures of α- and β-forms and the undesired α-isomer separated from the mixture at some stage, preferably at the stage mentioned hereinbefore, in conventional manner.

The pharmaceutically acceptable salts of the compounds of the present invention are prepared by simple reaction of the base compound of the invention with a pharmaceutically acceptable organic or inorganic acid.

The pharmaceutically acceptable solvates of the compounds of the present invention are prepared during the course of the preparation of the compound during its work up or during recrystallisation.

The invention also provides a pharmaceutical composition comprising a compound of formula (I), or a pharmaceutically acceptable salt thereof or a solvate thereof, and a pharmaceutically acceptable carrier.

Such compositions are prepared by admixture and are preferably adapted for oral or parenteral administration and as such may be in the form of tablets, capsules, oral liquid preparations, powders, granules, lozenges, reconstitutable powders, injectable and infusable solutions or suspensions or suppositories. Orally administerable compositions are preferred.

Tablets and capsules for oral administration are usually presented in a unit dose, and contain conventional excipients such as binding agents, fillers, tabletting agents, lubricants, disintegrants and wetting agents. The tablets may be coated according to well known methods in the art. Oral liquid preparations are usually in the form of aqueous or oily suspension, solutions, emulsions, syrups or elixirs or are presented as a dry product for reconstitution with water or other suitable vehicle before use. Such liquid preparations may contain conventional additives such as suspending agents, emulsifying agents, non-aqueous vehicles (which may include edible oils), preservatives and flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in the vehicle and filter sterilising before filling into a suitable vial or ampoule and sealing. Advantageously, adjuvants such as a local anaesthetic, preservatives and buffering agents are also dissolved in the vehicle.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform destribution of the compound of the invention.

The invention further provides a method of treatment of psychosis in mammals, such as humans, which comprises the administration of an anti-psychotic effective amount of a compound of the present invention, or a pharmaceutically acceptable salt or a solvate thereof, or a pharmaceutical composition, as hereinbefore defined, to the mammal.

An amount effective to treat the disorders hereinbefore described depends on the relative efficacies of the compounds of the invention, the nature and severity of the disorder being treated and the weight of the mammal. However, a unit dose will normally contain from 0.1 to 20 mg for example 0.5 to 10 mg, of the compound of the invention. Unit doses will normally be administered once, twice or thrice a day such that the total daily dose is normally in the range 0.01 to 10 mg/kg per day.

The invention also provides a compound of formula (I), or a pharmaceutically acceptable salt or solvate thereof, or a pharmaceutical composition, as hereinbefore defined, for use in the treatment of disorders of the central nervous system.

The following examples illustrate the preparation of compounds of the invention and the following descriptions illustrate the preparation of intermediates.

Description 1

3β-Acetylamino-9-benzyl-9-azabicyclo[3.3.1]nonane (D1)

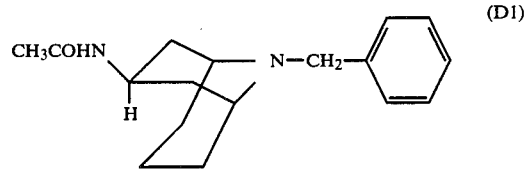

A solution of 3β-amino-9-benzyl-9-azabicyclo[3.3.1]nonane (7.2 g) and excess acetic anhydride in ethanol (100 ml) was stirred at room temperature for 48 hours. The solvent was evaporated and the residue dissolved in water and dichloromethane. It was basified with potassium carbonate and the dichloromethane extracted, separated, dried and evaporated to give 3β-acetylamino-9-benzyl-9-azabicyclo[3.3.1]nonane (6.5 g, 73%).

Description 2

3β-Acetylamino-9-azabicyclo[3.3.1]nonane (D2)

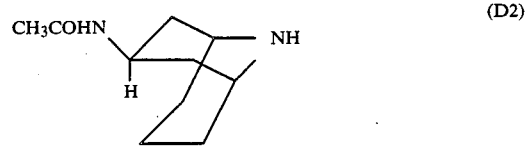

A solution of 3β-acetylamino-9-benzyl-9-azabicyclo[3.3.1]nonane (6 g) in ethanol (300 ml) was hydrogenated at room temperature and atmospheric pressure with 10% palladium on charcoal. The solution was filtered and the solvent evaporated to give the title compound (4.1 g, 100%).

Description 3

3β-Acetylamino-9-(4-fluorobenzyl)-9-aza-bicyclo-[3.3.1]nonane (D3)

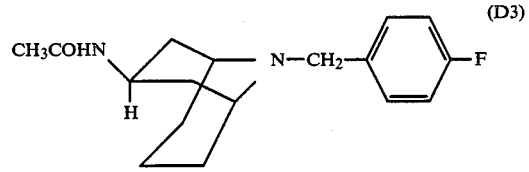

A solution of 3-β-acetylamino-9-azabicyclo-[3.3.1]nonane (3 g), 4-fluorobenzyl chloride (2.4 g) and potassium carbonate (4 g) in DMF (100 ml) was stirred at room temperature for 48 hours. The solution was evaporated and the residue dissolved in water. Extraction with ethyl acetate followed by evaporation of solvent afforded 3-β-acetylamino-9-(4-fluorobenzyl)-9-azabicyclo-[3.3.1]nonane (4.2 g, 90%).

Description 4

3β-Amino-9-(4-fluorobenzyl)-9-azabicyclo-[3.3.1]nonane (D4)

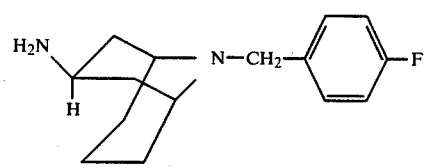

A solution of 3-β-acetylamino-9-(4-fluorobenzyl)-9-azabicyclo-[3.3.1]nonane (4.2 g) in ethanol (60 ml) and concentrated hydrochloric acid (10 ml) was heated at reflux for 24 hours. The solution was evaporated and the residue dissolved in water, basified with potassium carbonate and extracted with dichloromethane. Evaporation of solvent afforded 3-β-amino-9-(4-fluorobenzyl)-9-azabicyclo-[3.3.1]nonane (2.6 g, 72%) which was used in the next procedure without purification.

Description 5

9-(4-Fluorobenzyl)-9-aza-bicyclo-[3.3.1]-nonan-3-one (D5)

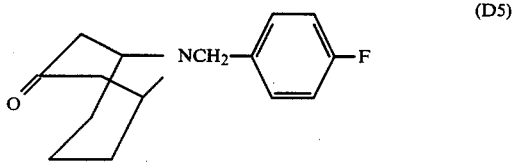

A solution of 4-fluorobenzylamine (25 g) in dilute hydrochloric acid (5N, 40 ml) was added to glutaric dialdehyde (50%, 48 ml) in water (800 ml) with stirring. A solution of 1,3-acetonedicarboxylic acid (29.2 g) and sodium acetate (16.4 g) in water (200 ml) was then added and the mixture stirred for 24 hours at room temperature. A further quantity of dilute hydrochloric acid (10 ml) was then added and the mixture stirred for a further 48 hours.

It was made acidic and the acid solution washed with ether. The acidic solution was then basified and extracted with ether. The ether extract was washed with water, dried and evaporated to give the crude ketone (32.5 g, 65%). This was purified by filtering a solution in ethyl acetate through alumina.

Description 6

9-(4-Fluorobenzyl)-9-aza-bicyclo-[3.3.1]-nonan-3-one oxime (D6)

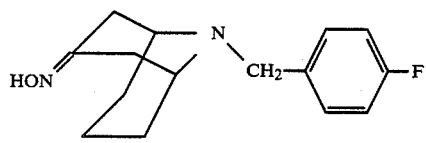

A solution of N-(4-fluorobenzyl)-9-aza-bicyclo-[3.3.1],nonan-3-one (32.5 g), hydroxylamine hydrochloride (9.5 g) and pyridine (5 ml) in ethanol (500 ml) was heated at reflux for 1 hour. The solution was evaporated and the residue dissolved in ethyl acetate and water. It was basified with potassium carbonate and the ethyl acetate extract was separated, dried and evaporated to give the crude oxime. Recrystallisation from ethyl acetate/light petroleum gave the oxime (26.7 g, 78%).

Description 7

3β-Amino-9-(4-fluorobenzyl)-9-azabicyclo[3.3.1]-nonane (D7)

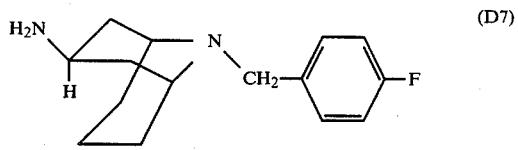

9-(4-Fluorobenzyl)-9-aza-bicyclo-[3.3.1]-nonan-3-one oxime (10 g) was dissolved in amyl alcohol (150 ml) and heated to reflux. Sodium (10 g) was added portionwise whilst the solution was stirred. After all the sodium had dissolved, the solution was cooled, diluted with ether and acidified with dilute hydrochloric acid. The acid extract was washed with ether and then basified with excess potassium carbonate. Extraction with ethyl acetate followed by evaporation of solvent afforded crude 3β-amino-9-(4-fluorobenzyl)-9-azabicyclo[3.3.1]-nonane (6.5 g, 70%) used in the next step without purification.

The amine of formula (D7) is predominantly one isomer and has the 3β-configuration.

Description 8

3β-Amino-9-(4-chlorobenzyl)-9-azabicyclo-[3.3.1]-nonane (D8)

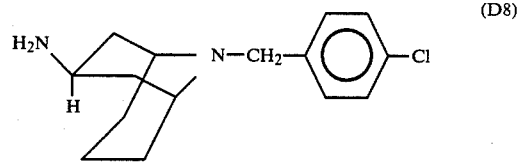

The title compound is prepared analogously to the preparation of the compound of Description 4.

Description 9

9-(4-Methylbenzyl)-9-aza-bicyclo-[3.3.1]-nonan-3-one (D9)

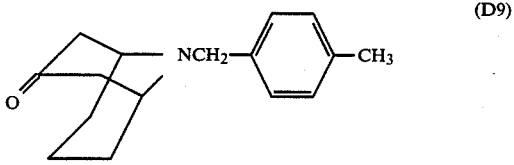

A solution of 4-methylbenzylamine (12 g) in dilute hydrochloric acid (5N, 20 ml) was added to glutaric dialdehyde (50%, 24 ml) in water (100 ml) with stirring. A solution of 1,3-acetonedicarboxylic acid (14.6 g) and sodium acetate (8.2 g) in water (100 ml) was then added and the mixture stirred for 24 hours at room temperature. A further quantity of dilute hydrochloric acid (5 ml) was then added and the mixture stirred for a further 48 hours.

It was made acidic and the acid solution washed with ether. The acidic solution was then basified and extracted with ether. The ether extract was washed with water, dried and evaporated to give the crude ketone. This was purified by filtering a solution in ethyl acetate through alumina. The yield was 13.5 g (56%).

Description 10

9-(4-Methylbenzyl)-9-aza-bicyclo-[3.3.1]-nonan-3-one oxime (D10)

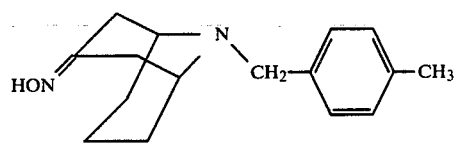

A solution of N-(4-methylbenzyl)-9-aza-bicyclo-[3.3.1]-nonan-3-one (5 g), hydroxylamine hydrochloride (1.5 g) and pyridine (0.75 ml) in ethanol (100 ml) was heated at reflux for 1 hour. The solution was evaporated and the residue dissolved in ethyl acetate and water. It was basified with potassium carbonate and the ethyl acetate extract was separated, dried and evaporated to give the crude oxime. Recrystallisation from ethyl acetate/light petroleum gave the oxime (4 g, 77%).

Description 11

3β-Amino-9-(4-methylbenzyl)-9-azabicyclo[3.3.1]-nonane (D11)

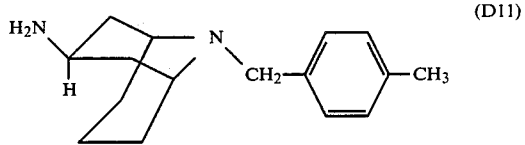

9-(4-Methylbenzyl)-9-aza-bicyclo-[3.3.1]-nonan-3-one oxime (4 g) was dissolved in amyl alcohol (100 ml) and heated to reflux. Sodium (2 g) was added portionwise whilst the solution was stirred. After all the sodium had dissolved, the solution was cooled, diluted with ether and acidified with dilute hydrochloric acid. The acid extract was washed with ether and then basified with excess potassium carbonate. Extraction with ethyl acetate followed by evaporation of solvent afforded crude 3-amino-9-(4-methylbenzyl)-9-azabicyclo[3.3.1]-nonane (3.6 g, 95%) used in the next procedure without purification.

This amine is predominantly one isomer and has the 3β-configuration.

EXAMPLE 1

(A)

4-Acetylamino-5-chloro-2-methoxy-N-{3'β-[9'-(4-fluorobenzyl)-9'-azabicyclo[3.3.1]-nonyl]}benzamide (E1A)

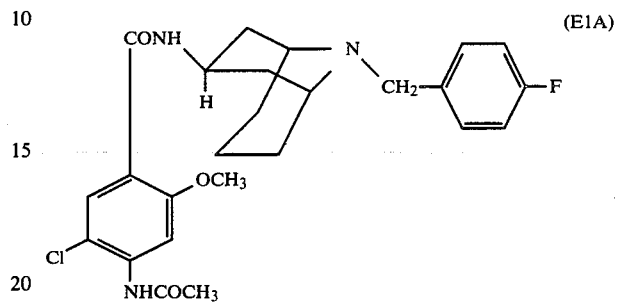

To 4-acetylamino-5-chloro-2-methoxy-benzoyl chloride (2.78 g) in dichloromethane (50 ml) and triethylamine (3 ml) was added 3β-amino-9-(4-fluorobenzyl)-9-azabicyclo-[3.3.1]-nonane (2.98 g) in dichloromethane (50 ml). The reaction mixture was stirred at room temperature for 30 minutes. It was then diluted with water, basified with potassium carbonate and extracted with dichloromethane. Evaporation of the dichloromethane extract gave a crude product which was chromatographed on alumina (neutral, grade II) using ether/ethyl acetate mixtures as eluant to give 4-acetylamino-5-chloro-2-methoxy-N-{3'β-[9'-(4-fluorobenzyl)-9'-azabicyclo[3.3.1]-nonyl]}-benzamide (3.4 g, 60%).

(B)

4-Amino-5-chloro-2-methoxy-N-{3'β-[9'-(4-fluorobenzyl)-9'-azabicyclo[3.3.1]-nonyl]}-benzamide (E1B)

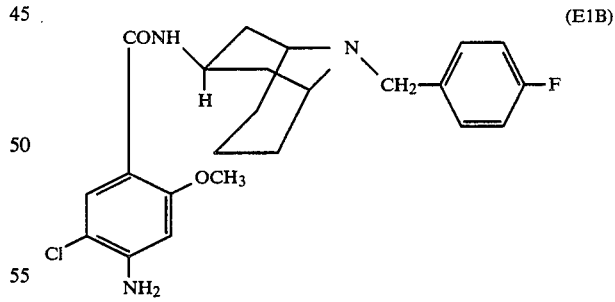

The product (3.4 g) of the above reaction was heated at reflux with potassium hydroxide (1.3 g) in ethanol (200 ml) and water (10 ml) for 2 hours. The mixture was then cooled and evaporated under reduced pressure. The residue was dissolved in dichloromethane and water. The dichloromethane extract was dried and evaporated to give a crude product which was recrystallised from ethyl acetate/light petroleum to give the title compound. (2.2 g, 71%) m pt: 221°–2° C.

EXAMPLE 2

(A)
4-Acetylamino-5-chloro-2-methoxy-N-{3'β-[9'-(4-chlorobenzyl)-9'-azabicyclo[3.3.1]-nonyl]}-benzamide (E2A)

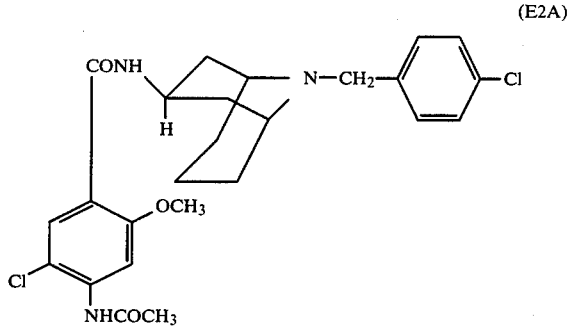

The title compound was prepared analogously to the preparation of the compound of Example 1A.

(B)
4-Amino-5-chloro-2-methoxy-N-{3'β-[9'-(4-chlorobenzyl-9'-azabicyclo[3.3.1]-nonyl]}-benzamide (E2B)

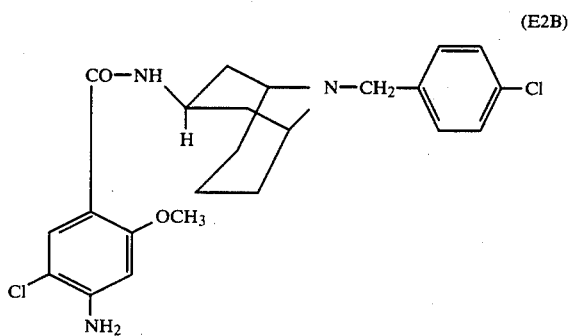

The title compound was prepared analogously to the preparation of the compound of Example 1B (m.p. 208°-10° C.).

EXAMPLE 3

(A)
4-Acetylamino-5-chloro-2-methoxy-N-{3'β-(9'-(4-methyl-benzyl)-9'-azabicyclo[3.3.1]-nonyl]}-benzamide (E3A)

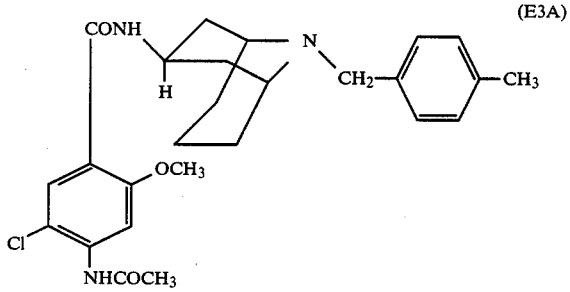

To 4-acetylamino-5-chloro-2-methoxy-benzoyl chloride (3.86 g) in dichloromethane (100 ml) and triethylamine (3 ml) was added 3β-amino-9-(4-methylbenzyl)-9-azabicyclo-[3.3.1]-nonane (3.6 g) in dichloromethane (100 ml). The reaction mixture was stirred at room temperature for 30 minutes. It was then diluted with water, basified with potassium carbonate and extracted with dichloromethane. Evaporation of the dichloromethane extract gave a crude product which was chromatographed on alumina (neutral, grade II) using ether/ethyl acetate mixtures as eluant to give 4-acetylamino-5-chloro-2-methoxy-N-{3'β-[9'-(4-methylbenzyl)-9'-azabicyclo[3.3.1]-nonyl]}-benzamide. (4.5 g, 65%).

(B)
4-Amino-5-chloro-2-methoxy-N-{3'β[9'-(4-methylbenzyl)-9'-azabicyclo[3.3.1]-nonyl]}-benzamide (E3B)

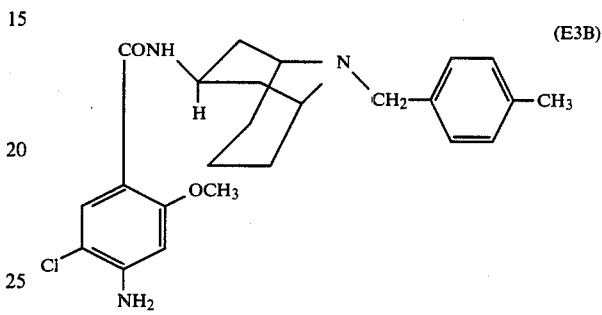

The product (4.5 g) of the above reaction was heated at reflux with potassium hydroxide (1.5 g) in ethanol (100 ml) and water (10 ml) for 2 hours. The mixture was then cooled and evaporated under reduced pressure. The residue was dissolved in dichloromethane and water. The dichloromethane extract was dried and evaporated to give a crude product which was recrystallised from ethyl acetate/light petroleum to give the title compound (3.07 g, 75%), m.p. 215°-6°.

EXAMPLE 4

4-Amino-5-bromo-2-methoxy-N-(3'β-[9'-(4-fluorobenzyl)-9'-azabicyclo[3.3.1]-nonyl])benzamide (E4)

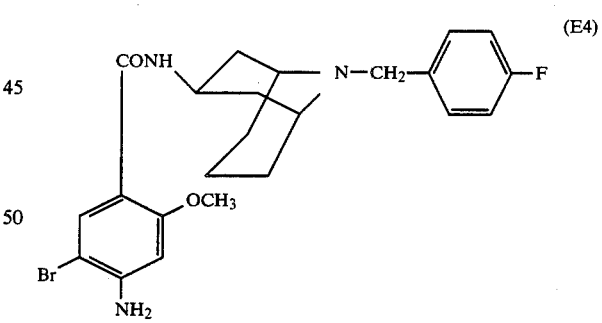

To 4-amino-5-bromo-2-methoxybenzoic acid (1.23 g) and triethylamine (0.7 ml) in dichloromethane (50 ml) was added ethyl chloroformate (0.5 ml) and the reaction mixture stirred at room temperature for 15 minutes. 3β-Amino-9-(4'-fluorobenzyl)-9-azabicyclo[3.3.1]nonane (1.24 g) in dichloromethane (10 ml) was added dropwise over 15 minutes and the reaction mixture stirred at room temperature for 1 hour. 10% Sodium hydroxide solution was then added and the dichloromethane separated and dried. Evaporation of the dichloromethane extract gave a crude product which was recrystallised from ethyl acetate to give 4-amino-5-bromo-2-methoxy-N-(3'β-[9'-(4-fluorobenzyl)-9'- azabicyclo[3.3.1]-nonyl])benzamide (1.4 g, 59%) m.p. 221°–3° C.

EXAMPLE 5

(A)

4-Acetylamino-2-methoxy-N-(3'β-[9'-(4-fluorobenzyl)-9'-azabicyclo-[3.3.1]-nonyl])-benzamide (E5A)

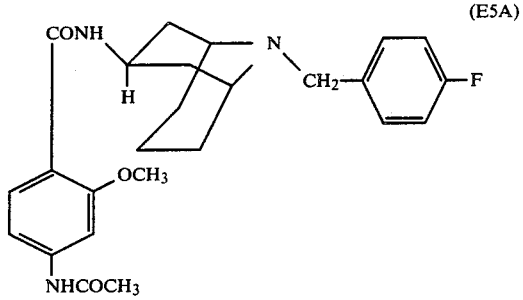

Following the procedure described for Example 4, 4-acetylamino-2-methoxy-benzoic acid (1.04 g) was converted to 4-acetylamino-2-methoxy-N-(3'β-[9'-(4-fluorobenzyl)-9'-azabicyclo-[3.3.1]-nonyl])-benzamide (1.2 g, 55%), m.p. 187°–189° C. Purification was carried out by chromatography on alumina (basic, Grade II) and elution with progressively graded mixtures of dichloromethane and ethyl acetate.

(B)

4-Amino-2-methoxy-N-(3'β-[9'-(4-fluorobenzyl)-9'-azabicyclo-[3.3.1]-nonyl])-benzamide (E5B)

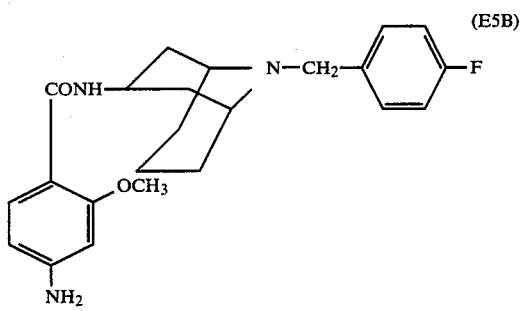

Following the procedure described for the preparation of the compound of formula E1B in Example 1 but using a reflux period of 18 hours, the compound of formula E5A (700 mg) was converted to the title compound (500 mg, 79%), m.p. 192°–3° C.

EXAMPLE 6

4-Acetylamino-5-chloro-2-methoxy-N-(3'β-[9'-(4-fluorobenzyl)-9'-azabicyclo-[3.3.1]-nonyl])-benzamide (E1A)

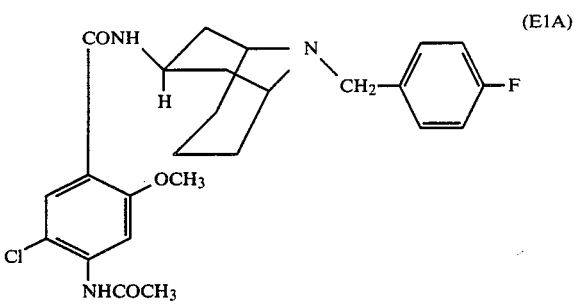

To 4-acetylamino-2-methoxy-N-(3'β-[9'-(4-fluorobenzyl)-9'-azabicyclo-[3.3.1]-nonyl])-benzamide (E5A) (400 mg) in acetic acid (5 ml) was added, dropwise with stirring, a solution of chlorine (70 mg) in acetic acid (1.5 ml). After 30 minutes, the solution was poured on ice, basified with potassium carbonate and extracted with ethyl acetate. The ethyl acetate extract was dried ($K_2CO_3$) and evaporated to give a crude product which was recrystallised from ethyl acetate/light petroleum to give the title compound (270 mg, 63%), m.p. 168°–169° C.

EXAMPLE 7

4-Amino-5-chloro-2-methoxy-N-(3'β-[9'-(4-fluorobenzyl)-9'-azabicyclo[3.3.1]-nonyl])-benzamide (E1B)

4-Nitro-5-chloro-2-methoxy-N-(3'β-[9'-(4-fluorobenzyl)-9'-azabicyclo[3.3.1]-nonyl])-benzamide is dissolved in ethanol and Raney nickel added. Hydrogenation is continued until the theoretical hydrogen uptake has taken place. The catalyst is filtered off and the filtrate evaporated. The residue is recrystallised from ethyl acetate/light petroleum to give the title compound.

PHARMACOLOGICAL DATA

The results in the following table are an illustration of the anti-psychotic activity of the present compounds as shown by Inhibition of Apormorphine Induced Climbing in the Mouse, a standard test.

Inhibition of apomorphine induced climbing in the mouse

The test is based on that described by Protais, P., Constantin, J. and Schwartz J. C. (1976), Psychopharmacology, 50, 1–6.

When mice are given a dose of 1 mg/kg apomorphine and then placed in an enclosed environment, such as an inverted wire cage, they are seen to climb around the walls. This behavioural phenomenon is thought to be a consequence of the stimulation of post-synaptic Dopamine (D.A.) receptors in the nucleus accumbens. Inhibition of apomorphine induced climbing is therefore indicative of post-synaptic D.A. receptor blockade in the accumbens.

Groups of 10 male CD1 mice, weighing 25–30 g were pre-treated orally with either graded doses of the test compound or vehicle, at appropriate time intervals before the subcutaneous administration of a sub-maximal dose of apomorphine (1 mg/kg). Immediately after the apomorphine injection the mice were placed in wire 'climbing cages' and each animal was scored for climbing behaviour at 10 and 20 minutes post apomorphine as follows:

Four paws on cage floor=0
Fore paws on cage wall=1
Four paws on cage wall=2

The total score was calculated for each group of mice and expressed as a percentage inhibition of climbing.

$$\% \text{ inhibition} = 100 - \frac{\text{Total score for test compound}}{\text{Total score for apomorphine control}} \times 10$$

ED50's and fiducial limits were calculated according to the method of Litchfield and Wilcoxon, the ED50 being the dose that produced a 50% inhibition of apomorphine-induced climbing.

The table shows the dose for 50% inhibition at 4 hour post dosing po.

| Compound of Example | $ED_{50}$ mg/kg |
| --- | --- |
| 1B | 0.008 |
| 2B | 0.027 |
| 3B | 0.07 |

TOXICITY

No toxic effects were observed in the test reported above.

What we claim is:

1. A compound of formula (XVII):

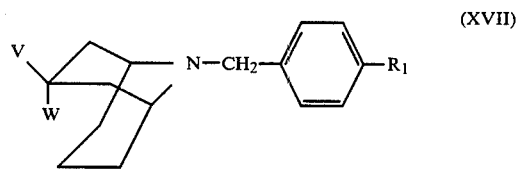

wherein V is amino or $C_{1-6}$ alkanoylamino and W is hydrogen or V and W together with the carbon atom to which they are attached are an oximino group, and $R_1$ is fluoro.

* * * * *